(12) United States Patent
Rambicourt et al.

(10) Patent No.: US 7,818,094 B2
(45) Date of Patent: Oct. 19, 2010

(54) CONTROL SYSTEM FOR MONITORING SALT LEVELS IN A BRINE TANK

(75) Inventors: James Rambicourt, Arnold, MO (US); Stephen Carpenter, High Ridge, MO (US)

(73) Assignee: Bio-Microbics, Inc., Shawnee, KS (US)

( * ) Notice: Subject to any disclaimer, the term of this patent is extended or adjusted under 35 U.S.C. 154(b) by 451 days.

(21) Appl. No.: 11/796,479

(22) Filed: Apr. 27, 2007

(65) Prior Publication Data

US 2008/0267824 A1 Oct. 30, 2008

(51) Int. Cl.
G01N 33/18 (2006.01)

(52) U.S. Cl. .................. 700/282; 700/281; 422/106; 422/112; 417/36; 417/38; 417/211.5; 417/297.5

(58) Field of Classification Search .................. 700/281, 700/282; 422/106, 112; 417/36, 38, 211.5, 417/297.5
See application file for complete search history.

(56) References Cited

U.S. PATENT DOCUMENTS

| | | | |
|---|---|---|---|
| 4,275,448 A * | 6/1981 | Le Dall ...................... 700/271 |
| 4,987,409 A * | 1/1991 | Jackson ...................... 340/623 |
| 5,297,428 A * | 3/1994 | Carr et al. .................. 73/290 R |
| 6,456,202 B2 * | 9/2002 | Johannsen et al. .......... 340/623 |
| 6,696,963 B2 * | 2/2004 | Zimmerman et al. ........ 340/612 |
| 6,696,966 B2 * | 2/2004 | Bearak ....................... 340/618 |
| 6,783,666 B2 * | 8/2004 | Takeda et al. .............. 210/96.1 |
| 2002/0091467 A1 * | 7/2002 | Rose et al. .................. 700/282 |

* cited by examiner

*Primary Examiner*—Jill Warden
*Assistant Examiner*—Shogo Sasaki
(74) *Attorney, Agent, or Firm*—Wood, Phillips, Katz, Clark & Mortimer

(57) ABSTRACT

A control system monitors salt level in a brine tank having a water inlet. The control system comprises a memory device storing an amount representing actual salt level in the brine tank. A sensor determines water level in the brine tank. A control valve is operatively connected between a water supply and the water inlet for controllably supplying water to the brine tank. A logic circuit is operatively connected to the memory device, the sensor and the control valve for determining salt level in the brine tank. The logic circuit periodically operates the control valve responsive to sensed water levels to fill the brine tank with water, updates the stored actual salt level in the memory device responsive to water supplied to the brine tank, and provides an indication when actual salt level in the brine tank falls below a select salt level.

13 Claims, 2 Drawing Sheets

CONTROL SYSTEM FOR MONITORING SALT LEVELS IN A BRINE TANK

CROSS REFERENCE TO RELATED APPLICATIONS

There are no related applications.

FIELD OF THE INVENTION

This invention relates to a control system for monitoring salt levels in a brine tank and, more particularly, to a non-invasive control system.

BACKGROUND OF THE INVENTION

Brine making tanks, also referred to herein as brine tanks, are used for various purposes, such as, for example, water softening. Such a tank is filled with salt and water to make brine. A commercial/industrial brine tank may be of any varying size according to requirements, with one example being about ten feet in height and fifteen feet diameter. Such a tank can hold about twenty-five tons of salt. The tank is periodically filled with water to form brine. Each time water is filled to the tank, a proportionate amount of salt is dissolved to gradually decrease level of salt in the tank. Once the salt has been dissolved, then it is necessary to refill the tank with salt.

It is important to know when the tank must be refilled with salt. Various procedures have been tried to gauge salt depth in brine tanks. These attempts have been made either on or in the brine tank itself.

One known system for monitoring salt level includes external markings on the tanks. However, due to variations in tank opacities, determining salt level and brine level can be unreliable. Ultrasonic devices have also been used. However, salt and water releases dissolved oxygen and tends to float certain air born insolubles into a foam on top of the liquid level. The ultrasonic device bounces a signal off of the top layer of the foam and cannot read the salt layer beneath the foam. The ultrasonic devices cannot differentiate between the semi-solid salt and the foam covering the liquid surface.

High intensity lamps may be used to illuminate the brine. However, salt when blown into the tanks may coat the lights and create high maintenance requirements as the lights must be cleaned often. The lights also add a great deal of heat into the enclosed space of the tanks. Plumb bob level indicators have been tried and are reasonably effective as long as an operator does not lower the plumb bob while filling the tank with salt. This leaves the plumb bob locked into the salt at a low point in the tank and cannot give a signal as long as it is buried in the salt. Finally, sight glasses have been tried but have two inherent problems. The first is that sight glasses are subject to breakage which drains the tank of all liquid brine. The second is that the salt tends to fill up the sight glass and requires periodic flushing to clear the column.

The present invention is directed to overcoming one or more of the problems discussed above in a novel and simple manner.

SUMMARY OF THE INVENTION

In accordance with the invention, there is provided a control system for monitoring salt levels in a brine tank which relies on clean water in a remote location.

Broadly, in accordance with one aspect of the invention, there is disclosed a control system for monitoring salt level in a brine tank having a water inlet. The control system comprises a memory device storing an amount representing actual salt level in the brine tank. A sensor determines water level in the brine tank. A control valve is operatively connected between a water supply and the water inlet for controllably supplying water to the brine tank. A logic circuit is operatively connected to the memory device, the sensor and the control valve for determining salt level in the brine tank. The logic circuit periodically operates the control valve responsive to sensed water levels to fill the brine tank with water, updates the stored actual salt level in the memory device responsive to water supplied to the brine tank, and provides an indication when actual salt level in the brine tank falls below a select salt level.

It is a feature of the invention that the memory device comprises a counter.

It is another feature of the invention that the sensor comprises a pressure switch sensing pressure at the water inlet.

It is still another feature of the invention that the logic circuit comprises a timing relay initiated by the pressure switch to control the valve for a select time period.

It is still a further feature of the invention to provide an indicator light controlled by the logic circuit to indicate when actual salt level in the brine tank falls below the select salt level.

It is still a further feature of the invention that the logic circuit provides a remote indication when actual salt level in the brine tank falls below the select level.

It is still another feature of the invention that the memory device comprises a counter storing a predetermined count of how many tank filling operations will deplete a select salt amount.

There is disclosed in accordance with another aspect of the invention a non-invasive control system for monitoring salt level in a brine tank having a water inlet line. The control system comprises a counter storing an amount representing actual salt level in the brine tank. A sensor is connected in the water inlet line for determining water level in the brine tank. A control valve is operatively connected in the water inlet line for controllably supplying water to the brine tank. A logic circuit is operatively connected to the memory device, the sensor and the control valve for determining salt level in the brine tank. The logic circuit periodically operates the control valve responsive to sensed water level to fill the brine tank with water, updates the stored actual salt level in the memory device responsive to water supplied to the brine tank, and provides an indication when actual salt level in the brine tank falls below a select salt level.

Further features and advantages of the invention will be readily apparent from the specification and from the drawings.

DETAILED DESCRIPTION OF THE INVENTION

Figure 1:
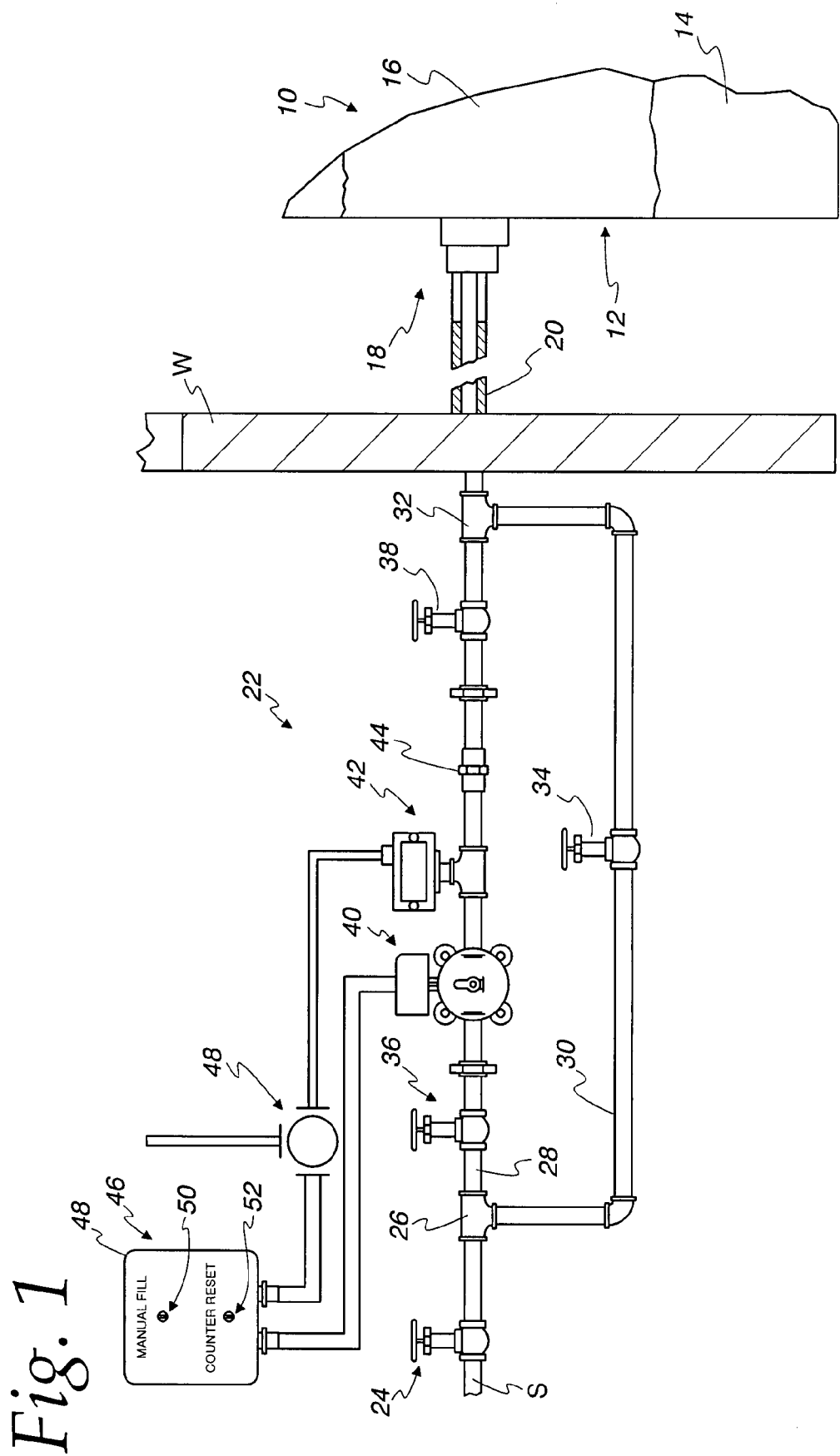
FIG. 1 is an elevation/hydraulic schematic of a non-invasive control system for monitoring salt level in a brine tank in accordance with the invention.

Referring initially to FIG. 1, a brine tank 10 includes a brine tank wall 12. The tank 10 may be of any desired size. In use, the brine tank 10 stores a supply of salt 14 and water 16 to form brine, as is known. The brine tank 10 is filled with salt 14 by any known means. A water inlet 18 is provided for filling the brine tank 10 with water. The water inlet 18 is connected to a water inlet line 20.

In accordance with the invention, a non-invasive control system 22 monitors salt level in the brine tank 10. The control system 22 is located in a remote location relative to the brine tank 10, as evidenced by a wall W disposed between the brine tank 10 and the control system 22. The control system 22 is non-invasive as it includes no structure in contact with the brine tank 10 and relies on clean water from a fresh water supply.

A first manual valve 24 connects to a fresh water supply line S. A T-coupling 26 connects the fresh water supply line S to a main line 28 and a bypass line 30. A second T-coupling 32 connects opposite ends of the main line 28 and bypass line 30 to the water inlet line 20. A second manual valve 34 is provided in the bypass line 30. Third and fourth manual valves 36 and 38 are provided in the main line 28 just inside the respective T-couplings 26 and 32, respectively.

The control system 22 comprises a solenoid valve 40 in the main line 28 downstream of the third manual valve 36. A pressure switch 42 is in the main line downstream of the solenoid valve 40. A flow control valve 44 is downstream of the pressure switch 42. In the exemplary embodiment of the invention, the flow control valve 44 limits flow rate in the main line to 30 GPM. Normally, the third manual valve 36 and the fourth manual valve 38 are open and the second manual valve 34 is closed. This operatively connects the main line 28 between the supply line S and the inlet line 20. For servicing or the like, the third manual valve 36 and the fourth manual valve 38 are closed and the second manual valve 34 is open. This operatively connects the bypass line 30 between the supply line S and the inlet line 20.

A logic controller 46 is electrically connected to the solenoid valve 40 and the pressure switch 42 and receives electrical power via a 115 volt AC source 48. The controller 46 comprises a housing 48 having a manual fill illuminated push button 50 and a counter reset illuminated push button 52. As described relative to FIG. 2, the manual fill illuminated push button 50 is conventional and includes a push button switch 50S and an indicator lamp 50L. Similarly, the counter reset illuminated push button 52 is conventional and includes a push button switch 52S and an indicator lamp 52L.

Figure 2:
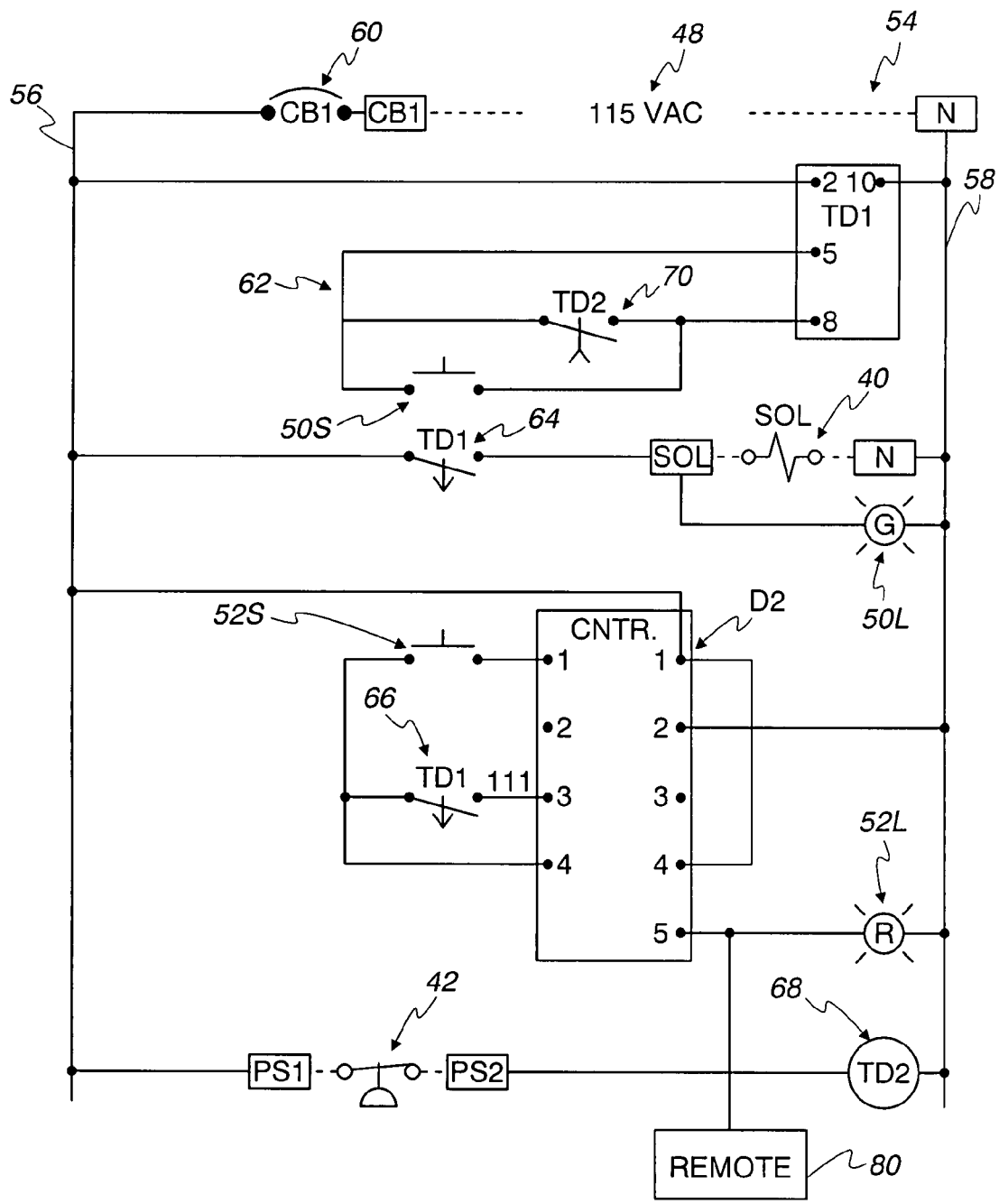
FIG. 2 is an electrical ladder diagram for the control system of FIG. 1.

Referring to FIG. 2, a ladder diagram illustrates an electrical schematic for a logic circuit 54 in the logic controller 46, see FIG. 1. The logic circuit 54 includes a power rail 56 and a neutral rail 58 connected to the AC supply 48 via a circuit breaker 60.

The logic circuit 54 comprises a first time delay relay TD1. The first time delay relay TD1 comprises a release delay relay, such as a Time Mark Model 381. The first time delay relay TD1 has power terminals 2 and 10 connected to receive power between the rails 56 and 58. An external control switching circuit 62 is connected between terminals 5 and 8 to control relay operation. The first time delay relay TD1 includes a first normally open contact 64 and a second normally open contact 66.

The logic circuit 54 comprises a second time delay relay TD2 having a coil 68. The second time delay relay TD2 may comprise a Time Mark Model 330 operate delay relay having a normally open contact 70.

The logic circuit 54 further comprises a memory device in the form of a counter 72 which may comprise a Red Lion Model LNXCC Lynx Contact Input Counter. An input side is shown to the left, while an output side is shown to the right. On the input side, the counter reset switch 52S is connected between a reset terminal 1 and a common terminal 4. The first time delay relay second normally open contact 66 is connected between the common terminal 4 and the count terminal 3. On the output side of the counter 72, power is provided at the output side terminals 1 and 2. The terminal 1 is also connected to output terminal 4. A relay output terminal 5 is connected to the manual fill lamp 50L.

The first time delay relay first normally open contact 64 is connected in series with the solenoid valve 40 between the rails 56 and 58. The manual fill indicator lamp 50L is connected in parallel with the solenoid valve 40.

The external control switching circuit 62 includes the manual fill push button switch 50S connected in parallel with the second time delay relay normally open contact 70 between terminals 5 and 8 of the first time delay relay TD1.

The pressure switch 42 is connected in series with the second time delay relay coil 68 between the rails 56 and 58.

In accordance with the invention, the brine tank 10 is selectively filled with a known quantity of salt. In an exemplary embodiment of the invention, the tank 10 may be filled with twenty-five tons of salt. By knowing how much water flows into the brine tank 10, the control system 22 can monitor salt level. Using the fact that one gallon of water dissolves 2.987 lbs. of salt, the counter 72 is set at a predetermined count of fills to gauge the salt level in the tank 10. For example, in an illustrated embodiment of the invention, the control system 22 is set to operate with a twenty minute fill time. At the controlled flow rate of 30 GPM, 600 gallons of water are used during a filling operation. This results in approximately twenty-eight filling operations to dissolve twenty-five tons of salt.

In one embodiment of the invention, the first time delay relay TD1 is set to remain actuated for twenty minutes to provide the twenty minute fill time. The second time delay relay TD2 provides an operation delay of thirty seconds. The pressure switch 42 being connected to the water inlet 18 senses water pressure, representing water level remaining in the tank above the water inlet 18. The pressure switch is set to actuate at a desired pressure level when a water filling operation should be commenced. When the pressure switch 42 is actuated, it opens the signal to the second time delay relay coil 68. After thirty seconds delay, the related contact 70 closes to actuate the first time delay relay TD1. This causes the contacts 64 and 66 to close. Closure of the first contact 64 energizes the solenoid 40 to open the solenoid valve on the fresh water inlet line for a preset period of time and illuminate the light 50L. The counter 72 is incremented responsive to closure of the second contact 66. By counting the number of times the first time delay relay TD1 is actuated, and controlling the number of gallons of fresh water that flows into the tank 10, the controller 46 monitors the salt level. When the counter 72 reaches the preset number of filling cycles, the warning light 52L illuminates on the housing 48. Additionally, or alternatively, a remote signal can be sent to a remote circuit 80 such as a remote warning light or using telemetry technology or Internet technology. When a new delivery of salt is received, the reset push button switch 52S is actuated to reset the counter 72 and turn off the warning light 52 L.

The use of the control system 22 allows a user an opportunity to install the unit in a remote, clean and environmentally monitored atmosphere. The remote location reduces the effects of extreme climates. Moreover, being connected only in the water inlet line removes the controls from the harsh salt and brine environment and reduces the frequency of physically checking salt levels resulting in less exposure to injury for personnel.

Thus, in accordance with the invention, there is described a non-invasive control system for monitoring salt level in a brine tank.

We claim:

1. A control system for monitoring salt level in a brine tank having a water inlet, comprising:
   a memory device storing an amount representing actual salt level in the brine tank;
   a sensor determining water level in the brine tank;
   a control valve operatively connected between a water supply and the water inlet for controllably supplying water to the brine tank; and
   a logic circuit operatively connected to the memory device, the sensor and the control valve for determining salt level in the brine tank, the logic circuit a) periodically operating the control valve responsive to sensed water level to fill the brine tank with water, b) updating the stored actual salt level in the memory device responsive to water supplied to the brine tank, and c) providing an indication when actual salt level in the brine tank falls below a select salt level.

2. The control system of claim 1 wherein the memory device comprises a counter.

3. The control system of claim 1 wherein the sensor comprises a pressure switch sensing pressure at the water inlet.

4. The control system of claim 1 wherein the logic circuit comprises a timing relay initiated by the pressure switch to control the valve for a select time period.

5. The control system of claim 1 further comprising an indicator light controlled by the logic circuit to indicate when actual salt level in the brine tank falls below the select salt level.

6. The control system of claim 1 wherein the logic circuit provides a remote indication when actual salt level in the brine tank falls below the select salt level.

7. The control system of claim 1 wherein the memory device comprises a counter storing a predetermined count of how many tank filling operations will deplete a select salt amount.

8. A non-invasive control system for monitoring salt level in a brine tank having a water inlet line, comprising:
   a counter storing an amount representing actual salt level in the brine tank;
   a sensor connected in the water inlet line for determining water level in the brine tank;
   a control valve operatively connected in the water inlet line for controllably supplying water to the brine tank; and
   a logic circuit operatively connected to the counter, the sensor and the control valve for determining salt level in the brine tank, the logic circuit a) periodically operating the control valve responsive to sensed water level to fill the brine tank with water, b) updating the stored actual salt level in the counter responsive to water supplied to the brine tank, and c) providing an indication when actual salt level in the brine tank falls below a select salt level.

9. The non-invasive control system of claim 8 wherein the counter stores a predetermined count of how many tank filling operations will deplete a select salt amount.

10. The non-invasive control system of claim 8 wherein the sensor comprises a pressure switch sensing pressure in the water inlet line.

11. The non-invasive control system of claim 8 wherein the logic circuit comprises a timing relay initiated by the pressure switch to control the valve for a select time period.

12. The non-invasive control system of claim 8 further comprising an indicator light controlled by the logic circuit to indicate when actual salt level in the brine tank falls below the select salt level.

13. The non-invasive control system of claim 8 wherein the logic circuit provides a remote indication when actual salt level in the brine tank falls below the select salt level.

* * * * *